United States Patent [19]

Ricchiuti

[11] Patent Number: Plant 6,488

[45] Date of Patent: Dec. 27, 1988

[54] NECTARINE TREE, P-R RED

[76] Inventor: Pat Ricchiuti, 2917 E. Shepherd Ave., Clovis, Calif. 93612

[21] Appl. No.: 34,916

[22] Filed: Apr. 6, 1987

[51] Int. Cl.[4] ..... A01H 5/00

[52] U.S. Cl. ..... Plt./41

[58] Field of Search ..... Plt./41

*Primary Examiner*—Robert E. Bagwill

*Attorney, Agent, or Firm*—Worrel & Worrel

[57] ABSTRACT

A new and distinct variety of nectarine tree which is somewhat similar to the September Grand Nectarine Tree (U.S. Plant Pat. No. 1,755) from which it was derived as a chance sport but which is distinguished therefrom and characterized as to novelty by producing fruit which is mature for commercial harvesting approximately September 3 through September 19 at Clovis, Calif. and which has excellent shipping and storage characteristics.

1 Drawing Sheet

BACKGROUND OF THE NEW VARIETY

The present invention relates to a new and distinct variety of nectarine tree denominated varietally as the "P-R Red", and more particularly to a Nectarine Tree which is generally similar in physical characteristics to the September Grand Nectarine Tree (U.S. Plant Pat. No. 1,755), of which it is a newly found sport, but from which it is distinguished as to novelty by bearing fruit which is ripe for commercial harvesting approximately September 3 through September 19 at Clovis, Calif., this date of harvest being approximately 5 to 7 days later than the September Grand Nectarine Tree which is generally ripe for commercial harvesting approximately the second week of September at Clovis, Calif.

The September Grand Nectarine Tree (U.S. Plant Pat. No. 1,755) is well known as a vigorous producer of large, firm flesh clingstone fruit which are ripe for commercial harvesting approximately the second week in September in the San Joaquin Valley of Central California. Furthermore, the fruit of the September Grand has long been known for its excellent eating quality, long shelf life and distinct aroma.

It has long been recognized that it would be desirable to have a nectarine tree which somewhat resembles the September Grand Nectarine Tree but which bears fruit which ripens for harvest later in the season whereby the commercial demand for such a late season nectarine can be supplied over a prolonged period of time.

ORIGIN AND ASEXUAL REPRODUCTION OF THE NEW VARIETY

The new and distinct variety of nectarine tree hereof was discovered as a chance sport on the applicant's property located at the corner of Bullard and Armstrong Avenues in Clovis, Calif. in September, 1972. The sport, which was found in a commercial planting of September Grand nectarines by the inventor, was noted at that time to have desirable characteristics. Bud wood from the sport was thereafter grafted into test trees by Mr. Glen Lewis, an employee of the applicant, on the same property located at the corner of Bullard and Armstrong Avenues in Clovis, Calif. This first asexual propagation which took place in January, 1973 has been continually observed by the applicant and it has been subsequently determined that this first grafting resulted in progeny being produced that were found to possess the same distinctive characteristics as the original sport.

SUMMARY OF THE NEW VARIETY

The P-R Red variety of nectarine tree is characterized by many of the desirable characteristics of the September Grand Nectarine Tree (U.S. Plant Pat. No. 1,755), but has the important distinction of bearing fruit that is different in coloration than that produced by the September Grand Nectarine Tree, and which is further ripe for commercial harvesting approximately September 3 through September 19; the September Grand Nectarine being usually ripe for commercial harvesting in the second week of September. The fruit of the new variety is clingstone by nature and has a flesh coloration that is light yellow with some reddish-pink coloration in the pit cavity and areas closely adjacent thereto.

BRIEF DESCRIPTION OF THE DRAWING

The accompanying drawing is a color photograph of six mature fruit of the subject variety, two of the mature fruit have been divided in the suture plane to show the flesh and pit characteristics, together with representative leaves which display the dorsal and ventral coloration thereof, and two pits, all of the subject variety.

DETAILED DESCRIPTION

Referring more particularly to the pomological details of this new and distinct variety of nectarine tree, the following has been observed under the ecological conditions prevailing at the applicant's commercial orchard which is located at the corner of Bullard and Armstrong Avenues in Clovis, Calif. All major color code identifications are by reference to "The Dictionary of Color" by Maerz and Paul, Second Edition, and in the alternative, the "Inter-Society Color Council, National Bureau of Standards." Common color names are also employed occasionally.

TREE

Size: Variable; medium to large.

Figure: Variable, upright, spreading and vase formed depending upon pruning practices.

Vigor: Average to vigorous.

Productivity: Productive.

Regularity of bearing: Regular.

Trunk:

*Size.*—Diameter in relation to length — average.
*Surface texture.*—Average.
*Color.*—Not distinctive.

Branches:
*Size.*—Generally — average.
*Texture.*—Medium, smooth.
*Color.*—Not distinctive.

Leaves:
*Size.*—Medium to large.
*Average length.*—Approximately 6½ inches, (165.1 mm.).
*Average width.*—Approximately 1¼ inches, (31.75 mm.).
*Form.*—Generally — lanceolate, acutely pointed.
*Thickness.*—Generally — average.
*Texture.*—Glabrous.
*Color — dorsal surface.*—Medium green, 23-J-8, (127. gy 01 G).
*Color — ventral surface.*—A pale green, 22-J-6, (120 m. YG).
*Marginal form.*—Crenate.
*Petiole.*—Length — average. Thickness — medium.
*Glandular characteristics.*—Numbers — generally — four are present; two are present on the blade, and two are present on the petiole.
*Position.*—Alternate.
*Size.*—Medium.
*Form.*—Reniform.

Flowers:
*Date of bloom.*—Generally — average as compared with other varieties; the flowers of the P-R Red are similar to the September Grand Nectarine Tree, from which it was derived as a sport.
*Size.*—Generally — large.
*Color.*—Pink.

FRUIT

Maturity:
*Ripe for commercial harvesting.*—September 3 through September 19 at Clovis, Calif.
*Maturity when described.*—Eating ripe — Sept. 19, 1986.

Size:
*Generally.*—Medium to large.
*Uniformity.*—*Uniform.*
*Average axial diameter.*—Approximately 2⅝ inches, (66.675 mm.).
*Average diameter transverse in the suture plane.*—approximately 2½ inches (63.5 mm.).

Form:
*Uniformity.*—Uniform.
*Symmetry.*—Symmetrical.
*Shape.*—Generally — globose.
*Suture.*—A distinct and deep suture extends from the base to beyond the apex with a slight depression evident beyond the pistil point.
*Ventral surface.*—Generally — strongly rounded.
*Stem cavity.*—Generally — rounded.
*Base.*—Shape — rounded.
*Apex.*—Generally — short and depressed.
*Pistil point.*—Wanting.

Skin:
*Thickness.*—Average.
*Texture.*—Medium to tough.
*Tenacious to flesh.*—Yes.
*Tendency to crack.*—Not observed.
*Pubescence.*—Wanting.
*Color.*—Approximately 10–20% of the entire surface is yellow, 10-K-5, (83. brill Y); 80–90% of the surface is red, which is somewhat variable in its shade, 6-L-5 through 7-L-5, (36 deep r O through 13 deep red).

Flesh:
*Juice production.*—Average to abundant.
*Texture.*—Firm, crisp and meaty.
*Ripening.*—Even.
*Flavor.*—Subacid.
*Aroma.*—Wanting.
*Eating quality.*—Fair to good.
*Color of flesh.*—Yellow, 9-L-4, (89. p y).
*Color of pit cavity.*—Red, 5-L-6, (14 v. deep Red).
*Color — flesh adjacent to the pit cavity.*—A lighter shade of red, (12. s Red).

Stone:
*Adhesion.*—Clingstone.
*Size.*—Generally — medium.
*Average length.*—Approximately 1⅜ inches, (34.528 mm.)
*Average width.*—Approximately 1 inch, (25.4 mm.).
*Average thickness.*—Approximately ⅝ inch, (15.875 mm.).
*Form.*—Oblong and globose.
*Base.*—Form — straight.
*Apex.*—Form — rounded.
*Sides.*—Generally — equal.
*Tendency to split.*—Not observed.
*Color.*—Reddish brown, 8-L-6, (40.s.r Br.).

Use: Fresh marker.
Keeping quality: Good.
Resistance to disease and insects: No unusual susceptibilities were noted.
Shipping quality: Excellent.

Although the new variety of nectarine tree possesses the desirable characteristics noted under the growing conditions prevailing in Clovis, Calif. in the central part of the San Joaquin Valley, it is to be understood that variations in the usual magnitude and in characteristics incident to changes in growing conditions, fertilization, pruning and pest control are to be expected.

Having thus described and illustrated my new variety of nectarine tree, what I claim as new and desire to secure by Plant Letters Patent is:

1. A new and distinct variety of nectarine tree substantially as illustrated and described which is characterized as to novelty by bearing a clingstone fruit having a yellow colored flesh, a skin color which is 80% to 90% red and by its general resemblance to the September Grand Nectarine Tree, U.S. Plant Pat. No. 1,755, from which it was derived as a chance sport, but from which it is distinguished therefrom by its bearing fruit which matures for harvesting approximately September 3 through September 19, later than the September Grand Nectarine Tree and by having excellent shipping and storage characteristics.

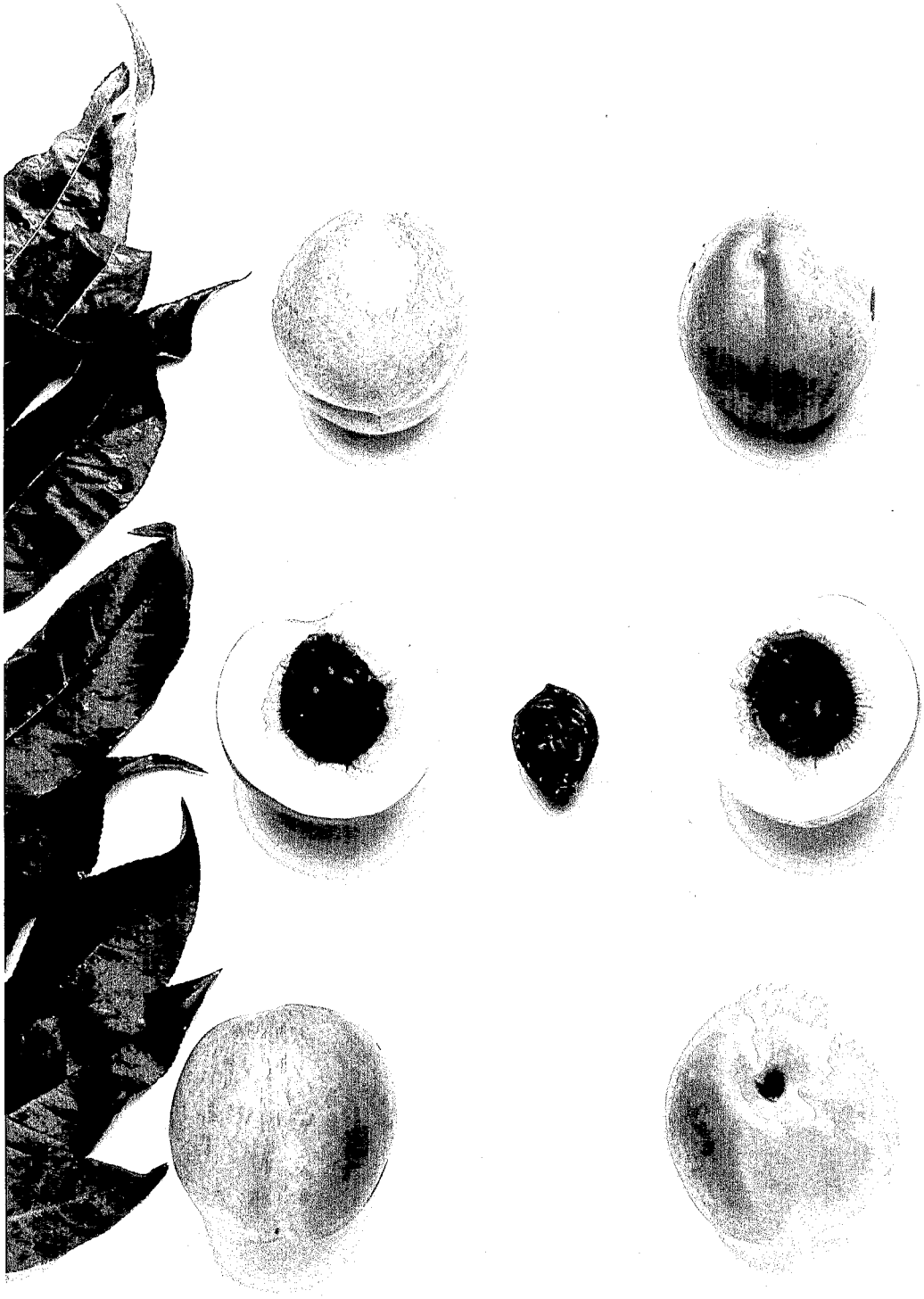

* * * * *